United States Patent [19]

Toth

[11] 4,064,452
[45] Dec. 20, 1977

[54] EDDY CURRENT DEFECT SIMULATOR AND METHOD

[75] Inventor: James Michael Toth, Lyndhurst, Ohio

[73] Assignee: Republic Steel Corporation, Cleveland, Ohio

[21] Appl. No.: 558,265

[22] Filed: Mar. 14, 1975

[51] Int. Cl.² ............................................. G01R 33/12
[52] U.S. Cl. ................................... 324/202; 324/238; 324/260
[58] Field of Search ............................. 324/37, 40, 41

[56] References Cited

U.S. PATENT DOCUMENTS

| 2,942,178 | 6/1960 | Nerwin .................................. 324/40 |
| 3,394,303 | 7/1968 | Cressman et al. ..................... 324/40 |
| 3,408,493 | 10/1968 | Westover et al. ..................... 324/41 |
| 3,652,928 | 3/1972 | Mansfield ............................. 324/41 |
| 3,823,368 | 7/1974 | Mansson et al. ..................... 324/40 |
| 3,826,976 | 7/1974 | Winston et al. ..................... 324/40 |

FOREIGN PATENT DOCUMENTS

| 226,922 | 9/1958 | United Kingdom ................... 324/40 |

OTHER PUBLICATIONS

Flaw Simulator for Probe Calibration, Instrument Technology, vol. 18, No. 4, Apr. 1971, p. 62.

Primary Examiner—Robert J. Corcoran
Attorney, Agent, or Firm—Watts, Hoffmann, Fisher & Heinke Co.

[57] ABSTRACT

A method and apparatus for calibrating an eddy current inspection system is disclosed which utilizes electronic workpiece flaw simulator circuitry for simulating a response produced by a flaw in a ferromagnetic calibration workpiece. The inspection system includes a detector probe which generates an electromagnetic field and is responsive to changes in the electromagnetic field. The workpiece flaw simulator circuitry is positioned in the electromagnetic field adjacent the detector probe. The workpiece flaw simulator circuitry controllably alters the electromagnetic field near the detector probe in a manner similar to a change in the field which would result from a workpiece having a defect of known severity passing through the field.

In a preferred embodiment, the workpiece flaw simulator circuitry includes a reaction coil and a resistive loading network which are coupled together to produce inductive and resistive components of impedance in the simulator circuitry. The loading network is adjustable to provide differing predetermined loadings on the reaction coil to the electromagnetic field sensed by the detector probe and thus simulate defects of known severity in the type of workpiece under test.

24 Claims, 3 Drawing Figures

EDDY CURRENT DEFECT SIMULATOR AND METHOD

BACKGROUND OF THE INVENTION

1. Field of the Invention

The present invention relates to eddy current inspection systems for detecting defects in ferromagnetic workpieces, and more particularly relates to a method and apparatus for calibrating such systems.

Eddy current inspection systems are well known for nondestructively inspecting ferromagnetic workpieces or products such as pipes, rods, tubes, etc. These systems have been particularly useful for locating anomalies, such as cracks, seams, laps, breaks and slivers in the workpiece which would not be discovered by visual inspection. The severity of anomalies varies greatly and in circumstances where an anomaly is of sufficient severity to adversely affect the function of the product when used for its intended purpose, the anomaly is, by definition, a defect.

Eddy current inspection systems generally operate by producing a varying electromagnetic field adjacent a localized area of the workpiece surface which in turn induces a localized pattern of electric eddy currents in the workpiece. The electromagnetic field is scanned along the workpiece by relatively moving the system and the workpiece. When the field is scanned across a defect in the workpiece, the defect changes the eddy current pattern. The eddy current pattern changes in turn alter the electromagnetic field and these field alterations are detected by the inspection system. The inspection system responds by marking the location of the defect in the workpiece or otherwise indicating that the defect is present. The degree of change of the eddy current pattern, and the resultant variation in the electromagnetic field, are proportional to the severity of the defect and, accordingly, eddy current inspection systems are capable of discriminating between anomalies, or defects, of differing severities.

One basic kind of eddy current inspection apparatus uses an electric coil for inducing the eddy currents in the workpiece (referred to as an "exciter" coil) and another electric coil (referred to as a "search" coil) which is positioned adjacent the location of the eddy currents in the workpiece for detecting changes in the electromagnetic field caused by changes in the eddy current pattern. An eddy current inspection system of this type is disclosed in U.S. Pat. No. 3,422,346, entitled EDDY CURRENT INSPECTION SYSTEM.

Another kind of eddy current inspection system has employed a single coil as both an exciter coil and a search coil. This type of single coil inspection system is disclosed by U.S. Pat. No. 3,688,186 issued to T. W. Judd, and entitled, METHOD AND APPARATUS FOR CURRENT FLAW DETECTION UTILIZING A DETECTOR WITH A POSITIVE AND TWO NEGATIVE FEEDBACK LOOPS (hereinafter the "JUDD patent"). In the system of the JUDD patent the coil is energized to induce eddy currents in the workpiece under test. The workpiece loads the coil to an extent determined by the nature of the workpiece and by workpiece defects which are located in the eddy currents. Changes in values of the coil loading caused by changes in the eddy current pattern produce changes in the energization of the coil and are detectable. The changes in the energization which are greater than a preset value are detected for initiating a defect signal which indicates that a defect has passed adjacent the probe coil.

During production, anomalies or slight imperfections are unavoidably produced in the workpieces. The intended usage of articles such as pipes and tubes often determines the severity of the anomalies which are allowable in the finished product. For example, when a pipe is to be subjected to high internal pressures, the existence of relatively minor anomalies in the pipe can substantially reduce the bursting strength of the pipe. On the other hand, if the pipe being inspected is not intended for use with high internal pressures, the pipe may contain relatively more severe anomalies without any adverse affects on its utility. Since eddy current inspection systems are used to inspecting different kinds of pipes and tubes, the systems must be capable of accurately detecting various degrees of severity of anomalies depending on the nature and/or the intended use of the product being inspected, so that anomalies which are sufficiently severe to constitute defects can be detected.

In the above noted inspection systems a defect signal proportional to the severity of the detected anomaly is produced. By adjusting the systems to respond to desired defect signal levels the systems are able to discriminate between degrees of severity of anomalies to indicate the presence of anomalies which are unacceptably severe, i.e., defects, for the particular kind of article being inspected. Since the difference between an acceptable anomaly and an unacceptable defect may be slight, it is essential that the systems be accurately adjustable.

In addition to the necessity for accurate adjustability of the systems, maintenance of the calibration of the systems, once adjusted, is essential. During operation the systems are occasionally exposed to changing environmental conditions, e.g., temperature changes, which tend to affect the accuracy of the systems. Similarly, wear and aging of various components tend to affect system accuracy over extended periods of use. Recalibration of the systems is therefore necessary from time to time.

THE PRIOR ART

Various techniques have been proposed for calibrating and adjusting the response of eddy current inspection systems. Early proposals included passing a sample, or calibration, workpiece having defects of known severities adjacent the defect detecting search coil. In some instances the sample workpieces contained natural defects, while in other cases defects were formed in standard workpieces by drilling holes or by attaching metallic slugs to the workpiece. These techniques required maintaining a store of sample workpieces corresponding to each type of workpiece to be inspected, with each workpiece containing defects of categorized severities.

The use of sample workpieces for calibrating the inspection systems have proven inconvenient partly due to the logistics involved. Furthermore, the sample workpieces were expensive, time consuming and burdensome to make and use.

In another prior art proposal an inspection system having separate exciter and search coils was provided with electronic control circuitry by which the exciter coil was energized by electronically controlled signals in order to simulate defects. In these systems a defect-free calibration workpiece was positioned adjacent the exciter and search coils, and the controlled energization of the exciter coil created a magnetic field having characteristics which influenced the search coil response in a manner which corresponded to the search coil response to a defect in the workpiece. The electronic control circuitry formed an integral part of the inspection systems and was adjustable to provide for differing predetermined exciter coil energizing signal levels in order to simulate defects of differing predetermined severities.

The latter mentioned prior art systems required relatively complicated electronic control circuitry for producing the exciter coil energizing signals. The distance between the exciter coil and the workpiece varied as a result of usage of the system, e.g., as a result of abrasion or wearing of the search coil supporting structure, causing variations in system sensitivity. As the system sensitivity varied, the electronic control circuitry required adjustment. Moreover, calibration of these systems required compensatory adjustment. Moreover, calibration of these systems required use of a defect-free calibration workpiece typical of the workpieces to be inspected. Furthermore, this prior art proposal was not subject to widespread use in testing because pre-existing inspection systems had to be substantially modified in order to incorporate the required electronic control circuitry. In general, the described prior art electronically controlled calibration systems have not provided an optimum solution of problems relating to calibration of eddy current inspection systems.

SUMMARY OF THE INVENTION

The present invention provides a new and improved method and apparatus for calibrating an eddy current inspection system by which workpiece defects of predetermined known severity are simulated by passive electrical simulator circuitry to enable calibration of the inspection system without requiring the use of any calibration workpieces and without requiring modification of the eddy current inspection system itself.

In accordance with the invention workpiece flaw simulator circuitry is inductively coupled to the electromagnetic field produced by a probe assembly of an eddy current inspection system and the impedance of the simulator circuitry is controllably altered to, in turn, alter the electromagnetic field. The magnitude of the change in the field produced by the simulator circuitry corresponds to the magnitude of the field change caused by a defect of known severity in a workpiece being inspected so that the eddy current inspection system can be accurately calibrated. The change in simulator circuitry impedance is adjustable so that workpieces with defects having differing known degrees of severity are simulated thus enabling the inspection system to be set to respond to the presence of such defects in actual workpieces being inspected.

In a preferred embodiment of the invention the simulator circuitry includes an inductor coil, a resistive loading network connected to the coil and a switch which is operated between open and closed conditions to effectively alter the impedance of the loading network. When the switch is in one condition the inductor coil and loading network cooperate so that the loading imposed on the probe assembly by the simulator circuitry, via the electromagnetic field, is at a predetermined level. When the switch is operated to its other condition the loading imposed on the probe assembly is altered to a second predetermined level. The difference between the probe assembly loading levels corresponds to the difference in loading of the probe assembly created during the inspection of a workpiece when a defect being a known degree of severity is encountered in the workpiece.

The resistive loading network is connected in series with the inductor coil and includes a plurality of resistive elements. The switch is associated with the network so that when the switch is in one of its conditions the resistance of at least one of the resistive elements is effectively removed from the simulator circuitry, thus altering the impedance of the simulator circuitry to an extent governed by the resistive impedance of the loading network element removed from the simulator circuitry.

The loading network element whose resistance is removable from the simulator circuitry by operation of the switch is preferably formed by a manually adjustable potentiometer. The potentiometer is adjustable as a function of the degree of severity of defect which is desired to be simulated by the simulator circuitry. This enables the inspection system operator to set the simulator circuitry to simulate a defect having a desired degree of severity and then to calibrate the inspection system to respond appropriately to that defect.

In a preferred embodiment of the invention the simulator circuitry is contained within two relatively small, portable housings. The inductor coil is disposed within one housing which is constructed so that it can be detachably supported on the probe assembly during calibration.

The loading network and switch are situated in the other housing and are connected to the inductor coil by a suitable cable arrangement including a connector which permits alternate inductor coils and their housings to be used with a common loading network housing.

The switch is preferably a solid-state electronic switch and in the preferred embodiment is associated with a control section circuit including a variable frequency oscillator having a manually adjustable frequency control potentiometer. The oscillator generates switch operating signals which are processed in the control section circuit for altering the conductive condition of the switch at a desired rate to produce a series of simulated defects which are coordinated in time with the calibration routine of the particular inspection system being calibrated. The oscillator is disposed in the loading network housing.

It is thus an object of the present invention to provide a novel and improved calibration apparatus and method using electronic workpiece simulator circuitry for simulating a calibration workpiece flaw to calibrate an eddy current inspection system.

Other features, advantages and objects will be apparent from the following detailed description when read in conjunction with the accompanying drawings.

DESCRIPTION OF A PREFERRED EMBODIMENT

Figure 1:
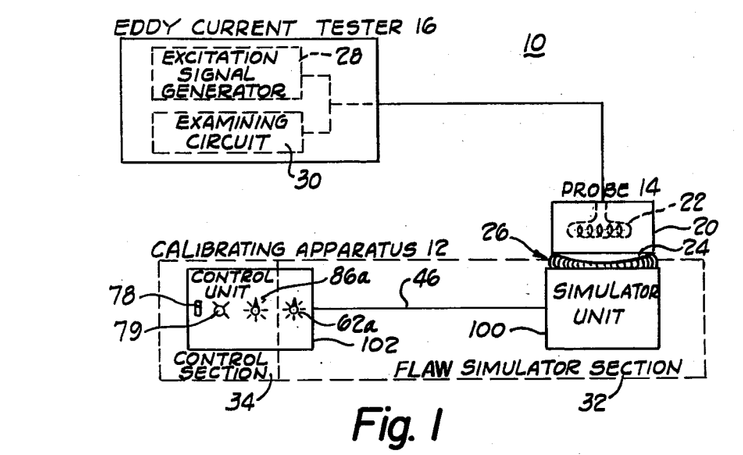
FIG. 1 is a functional block diagram of an eddy current inspection apparatus and a calibrating apparatus according to the invention.

FIG. 1 schematically illustrates an eddy current inspection system 10 associated with a calibrating apparatus 12 constructed according to the invention. The inspection system 10 may be of any suitable type but for the purpose of description the system 10 is of the type disclosed by the JUDD patent in which a single coil is utilized both as an exciter coil and a defect searching coil. The various components of the system 10 may be of suitable or conventional construction and therefore are illustrated schematically and only briefly described.

The eddy current inspection system 10 comprises a detector probe assembly 14 coupled to an eddy current tester unit 16. During inspection the detector probe assembly 14 is positioned adjacent a workpiece (not shown) for examining the workpiece for defects. Relative movement of the probe assembly 14 and the workpiece, which may be a pipe, a billet, etc., allows desired portions of the workpiece to be examined. When a defect in the workpiece passes within the region of examination established by the probe assembly 14 the defect is detected and its presence is appropriately indicated by the tester unit 16.

The probe assembly 14 comprises a housing 20 which encloses a probe coil 22 and a wear shoe 24 connected to the housing 20. During the inspection procedure the probe assembly 14 is positioned so that the wear shoe 24 engages and rides on the workpiece. The wear shoe is constructed from an abrasion resistant material and maintains the probe coil 22 spaced a predetermined distance from the workpiece surface.

The probe coil 22 is energized by a high frequency excitation signal from the tester unit 16 for establishing a localized intermittent electromagnetic field, indicated by the reference character 26, adjacent a surface region of the workpiece under test. The magnetic field 26 induces eddy currents in the workpiece which in turn produce an inductive load on the probe coil 22.

When the magnetic field is adjacent a workpiece region which is defect-free the eddy currents form a particular consistent pattern in the workpiece and the probe coil 22 has a determinable consistent inductive loading. As the probe coil 22 and the workpiece move relative to each other and a workpiece region containing a defect moves into the field 26, the eddy current pattern is altered by the defect which in turn alters the loading on the probe coil 22. The probe coil loading changes are detected by the tester unit 16 so that the presence of the defect is detected.

The illustrated eddy current tester unit 16 includes an excitation signal generator 28 connected to the probe coil 22 and an excitation signal examining circuit 30 which detects changes in the amplitudes of the excitation signal. The signal generator 28 is formed by suitable circuitry which generates the high frequency excitation signal to the probe coil 22. The examining circuit 30 detects changes in amplitude of the excitation signal resulting from changes in the inductive loading on the probe coil 22.

The magnitude of the loading change on the probe coil 22 varies proportionally with the severity of the workpiece defect located in the field 26 and produces a corresponding change in the excitation signal amplitude. The examining circuit 30 is adjustable to establish a threshold level of excitation signal change for indicating the presence of an unacceptably severe workpiece defect. Variations in the excitation signal amplitude which exceed the preset examining circuit threshold level cause the examining circuit to produce a defect signal.

The system 10 is constructed and arranged to respond to defect signals by suitably indicating the presence of the defect in the workpiece. For this purpose the system 10 may be provided with workpiece marking devices, not shown, for marking the workpiece in the vicinity of the detected defect.

The calibrating apparatus 12 is used with the system 10 in order to enable adjustment, or calibration, of the examining circuit 30 to produce defect signals in response to changes in the probe coil excitation signal levels which exceed a predetermined threshold change value. The examining circuit 30 may be calibrated from time to time during inspection of a series of identical workpieces and is calibrated each time it is desired to change the degree of severity of a defect to which the system 10 is to respond.

The preferred and illustrated calibrating apparatus 12 comprises a workpiece flaw simulator section 32 and a control section 34. During calibration of the system 10 the workpiece flaw simulator section 32 is coupled to the probe assembly 14 within the electromagnetic field 26 and the simulator and control sections cooperate to change the loading on the probe coil 22 in a manner corresponding to the change in the probe coil loading which would be occasioned by a workpiece containing a defect of known severity.

Figure 2:
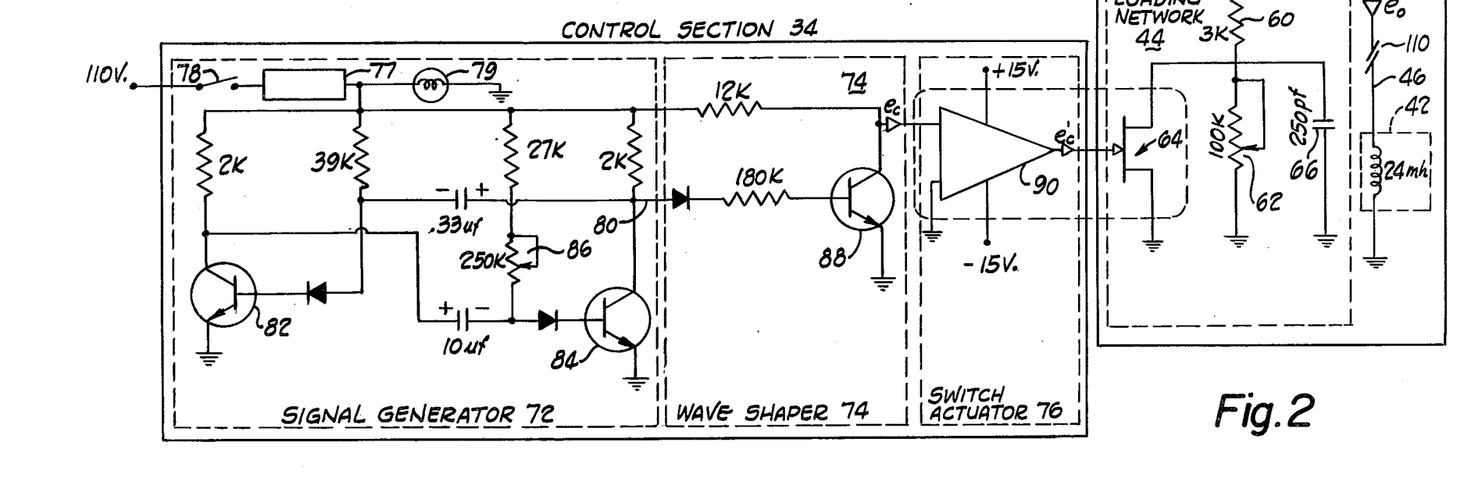
FIG. 2 is a circuit schematic of the calibrating apparatus of FIG. 1.

Referring to FIG. 2, the workpiece flaw simulator section 32 includes simulator circuity which is effective to inductively load the probe coil 22 during calibration and to controllably change the probe coil loading. The simulator circuitry comprises and inductor 42 and an inductor loading network 44 which cooperate to load the probe coil 22 during calibration.

The inductor 42 is preferably formed by a reaction coil which is positioned in the electromagnetic field 26 and inductively coupled to the probe coil 22 during calibration. The reaction coil is sized and configured to correspond to the respective size and configuration of the probe coil 22 to optimize the inductive coupling of the coils. In the preferred embodiment of the invention the reaction coil 42 is identical to the probe coil 22, and a replacement probe coil may be utilized as the reaction coil.

The inductor loading network 44 provides a controllably variable primarily resistive loading to the reaction coil 42 and thus controls the degree of loading of the probe coil 22 provided by the simulator circuitry. The loading network 44 comprises a resistor 60, a variable value resistor in the form of a potentiometer 62, a switch 64, and a capacitor 66. The fixed resistor 60 is connected in series with the reaction coil via a line 46. The loading potentiometer 62, the switch 64 and the capacitor 66 are connected in parallel with each other and in series between circuit ground and the resistor 60.

The switch 64 is operated between its opened and closed conditions to vary the loading imposed on the reaction coil 42 by the loading network. When the switch 64 is in its closed condition the reaction coil 42 and the resistor 60 are connected to circuit ground through the switch 64 so that the resistance of the potentiometer 62 is effectively removed from the loading network and has no effect on the loading of the reaction coil. The load on the reaction coil 42 is thus maximized when the switch is in its closed condition.

The value of the resistor 60 preferably provides a relatively high resistive loading on the reaction coil 42 and thus on the probe coil 22 when the switch 64 is in its closed condition. The particular value of the fixed resistor 60 is chosen so that the loading of the probe coil produced by the reaction coil 42 and the resistor 60 will allow a large enough transition when the circuit is opened to produce a change approximately equal in magnitude to the change produced by the largest defect to be expected to be simulated.

When the switch 64 is in its opened condition the inductor 42 is connected to circuit ground through the resistor 60 and the potentiometer 62 to reduce the load on the inductor 42 from the maximum level to a level determined by the setting of the potentiometer 62. The particular resistance value selected for the loading potentiometer 62 is chosen so that when the switch 64 is operated to its opened condition the potentiometer produces a change in resistive loading on the reaction coil 42 which results in a change in the loading on the probe coil 22 corresponding to that which would be caused by a defect of known severity in a workpiece being inspected.

The loading potentiometer 62 is preferably constructed to provide a relatively wide range of selectable resistive values. When the value of resistance provided by the potentiometer 62 is large, the change in resistive loading on the reaction coil 42 and hence the loading on the probe coil 22, is likewise large. Accordingly the change produced in the probe excitation signal value, as monitored by the excitation signal examining circuit 30, is substantial.

The capacitor 66 is coupled to the switch 64 for suppressing transient voltages produced by operation of the switch 64 and as such does not introduce an appreciable capacitive reactance into the loading network. The switch 64 is schematically illustrated in FIG. 2 and may be of any suitable construction, for example the switch could be formed by relay contacts or by a semiconductor device.

Figure 3:
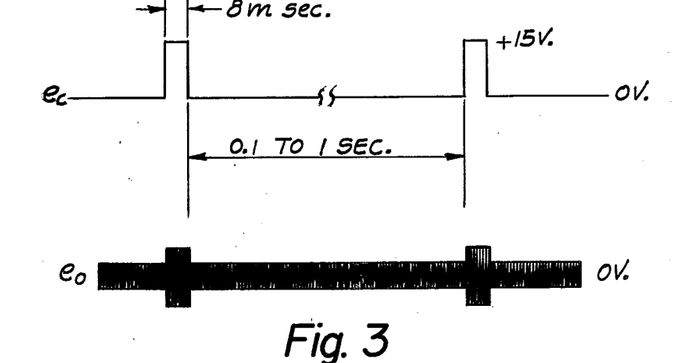
FIG. 3 illustrates a pair of waveforms characteristically produced by the calibration apparatus of FIG. 2.

The waveform denominated $e_o$ in FIG. 3 is illustrative of the voltage on the line 46 between the inductor 42 and the resistor 60 relative to circuit ground (assumed to be zero volts) during calibration of the inspection system 10. The signal $e_o$ represented in FIG. 3 comprises an amplitude modulated signal having a high frequency component at the frequency of the high frequency excitation signal of the probe assembly 14. The signal $e_o$ is modulated by operation of the switch 64 between its open and closed conditions and has an amplitude differential corresponding to the resistance of the loading potentiometer 62.

Operation of the switch 64 is controlled by the control section 34 which generates a switching signal $e_c$ (FIG. 3) having a high logic state which effectively operates the switch 64 to its open condition and a low logic state which operates the switch 64 to its closed condition. The control section 34 comprises a signal generator 72, a wave shaper 74 coupled to the signal generator 72, and a switch actuator circuit 76 which couples the wave shaper 74 to the switch 64 and provides a switching signal $e'_c$ corresponding to the signal $e_c$. A suitable low-voltage regulated DC power supply 77, controlled by an on-off switch 78, is connectable to the control section 34 and a pilot light 79 to provide operating power for the control section.

The signal generator 72 is preferably an oscillator formed by a conventional astable multivibrator which produces an asymmetrical oscillatory output signal on an output line 80. The signal generator 72 includes a pair of cross-coupled transistors 82, 84 and a timing network. The collector of each transistor is coupled to the base of the other transistor so that when one transistor is rendered conductive the other transistor is rendered nonconductive. The timing network is coupled to the transistors 82, 84 for diverting base drive current from the conductive transistor at a controlled rate to eventually render it nonconductive, thereby driving the other transistor conductive and causing oscillation.

The timing network includes a frequency control potentiometer 86 which is diode coupled to the base of the transistor 84 and determines the frequency of oscillation of the signal generator 72 by altering the time constant which controls the turn-on time of the transistor 84. The cross coupling between the transistors 82, 84 and the timing network provide a constant turn-on time to the transistor 82, resulting in the output signal on the line 80 to appear as a series of pulses having a substantially constant duration but a variable repetition rate. Because each pulse eventually causes a defect simulation to be presented to the system 10, the duration of each pulse is selected in accordance with characteristics of the detector probe assembly 14 and the scanning rate of the inspection system 10 at which the workpieces are scanned during test.

For the component values shown, each pulse from the signal generator 72 has a duration typically on the order of 8 milliseconds. Eight milliseconds has proven a desirable pulse width when used with an 0.24 inch (0.61 cm) diameter probe coil 22 having 24 millihenrys of inductance and which is scanned over the workpiece at a scan rate of approximately 70 feet per minute (21.3 meters per min.). A higher scan rate or a smaller search probe would ideally require a duration less than 8 milliseconds.

By varying the frequency of oscillation the frequency control potentiometer 86 controls the period between pulses, with the period adjustable between 0.1 and one second for the values shown. The particular setting of the frequency control potentiometer 86 is selected to establish an output signal having a pulse repetition rate which produces a series of simulated defects which occur at a rate corresponding to the scan rate at which the particular inspection system 10 is set.

The wave shaper 74 comprises an inverting output transistor 88 having its base coupled to the output line 80 of the signal generator 72 by a series connected diode-resistor combination. The collector of the transistor 88 is coupled to the switch actuator 76 and provides the signal $e_c$.

The switch actuator circuit 76 comprises circuitry shown schematically as an amplifier 90 for actuating the switch 64. The amplifier 90 represents any of various components which operate to actuate a switch; for example, a relay coil for operating a relay contact or an amplifier for operating a transistor, an SCR or the like. A preferred switch actuator 76 is integral with the switch 64 and is a so-called analog gate, commercially available as an integrated circuit sold under the designation DG200.

In the preferred embodiment the workpiece flaw simulator circuitry and the control circuitry are housed within a workpiece flaw simulator housing unit 100 and a control housing unit 102. The inductor 42 is disposed within the housing unit 100, while the loading network 44 and the control section 34 are both disposed in the control unit 102. The housing unit 100 is relatively small and is constructed so that it is easily secured to the housing 20 of the probe assembly 14. The housing unit 102 is coupled to the housing unit 100 by the line 46 and can thus be located a desirable distance away from the probe assembly 14 at a position which is convenient for the operator. For example, the housing unit 102 can be placed adjacent an operator control panel for the inspection system 10.

As shown in FIG. 1, the control housing unit 102 supports the on-off switch 78, the pilot light 79, a knob 86a for adjusting the wiper terminal of the frequency control potentiometer 86, and a knob 62a for adjusting the wiper terminal of the loading potentiometer 62. Mounting the switch 78, the light 79, and the control knobs 62a and 86a on the housing unit 102 permits easy operation of the calibrating apparatus 12 including adjustments of the control section 34 and simulator circuitry by the operator at the inspection system control panel so that the operator can remain at the control panel during the calibration procedure.

The ability to adjust the simulator apparatus via the potentiometer knob 62a on the control unit 102 is particularly beneficial when the eddy current inspection system 10 is of a type which detects and classifies several degrees of defects during a single operation (such as, for example, the system disclosed by U.S. Pat. No. 3,688,186, METHOD AND APPARATUS FOR EDDY CURRENT FLAW DETECTION UTILIZING A POSITIVE AND TWO NEGATIVE FEEDBACK LOOPS, issued Aug. 29, 1972). In such a system several threshold change levels may be programmed into the examining circuit 30 for comparison with excitation signals without requiring the operator to leave the control panel.

It should be appreciated that calibrating an eddy current inspection system having several defect classifications requires only a single placement of the simulator housing unit 100 on the probe assembly 14. The loading potentiometer 62 is then merely adjusted in sequence to each of the appropriate markings for establishing the associated threshold change levels.

Markings on a dial on the face of the control housing unit 102 are empirically correlated to various settings of the loading potentiometer 62 which correspond to defects of known severities. By directing dialing the wiper terminal knob 62a to the appropriate dial marking, the simulator unit 100 is easily programmed to simulate a desired degree of workpiece defect.

Yet another advantage in the dual housing construction of the simulator apparatus resides in the fact that the control housing unit 102 may be disconnected from one simulator housing unit 100 and reconnected to another simulator housing unit. Since different inspection system probe assemblies may have distinct probe coil configurations, optimum magnetic coupling and transient response can require conforming configurations in the reaction coil 50 used in the simulator apparatus. That is to say, a simulator housing unit 100 should have a reaction coil 50 configured to correspond to that of the probe coil 22 in the inspection system being calibrated. To facilitate exchanging the simulator housing unit 100, a quick disconnect connector 110 is provided in the line 46 between the simulator housing unit 100 and the control housing unit 102.

Although a preferred embodiment of the invention is illustrated and described in detail, the invention is not to be considered limited to the precise construction disclosed. Various adaptations, modifications and uses of the invention may occur to those skilled in the art to which the invention relates and the invention is to cover all such adaptations, modifications and uses which come with the scope or spirit of the appended claims.

What is claimed is:

1. A workpiece flaw simulator for facilitating calibration of an eddy current inspection system having a probe operable to produce varying electromagnetic fields for inducing eddy currents in a ferrous workpiece in said fields and which responds to changes in impedance loading of the probe caused by the presence of the ferrous workpiece in the fields, the flaw simulator comprising: first passive non-balanceable circuit means inductively couplable to said probe for loading said probe to a first degree independently of a coupling to the first circuit means and the probe of workpiece material, and second circuitry connected to said first circuit means for altering the effective impedance of said first circuit means as seen by said probe to vary the loading of the probe to simulate the introduction into the field of a ferrous workpiece having a defect of predetermined severity.

2. The apparatus according to claim 1 wherein said first circuit means comprises an inductor and said second circuit means comprises a loading network having impedence elements connected to said inductor.

3. Apparatus as claimed in claim 2 wherein said loading network comprises switch means having first and second conditions of conduction, said switch means coupled to said impedance elements and operable between said conditions to vary the amount of impedance effectively in said loading network.

4. The apparatus according to claim 3 wherein said loading network further comprises a fixed value resistor, and a variable value resistor, said switch means operable from said first state to said second state to effectively remove the resistance of said variable value resistor from said loading network.

5. The apparatus claimed in claim 4 wherein said variable value resistor is connected to a manually adjustable member for governing the impedance value of said variable value resistor, said member adjustable to control the extent the impedance of said simulator circuitry is altered by said switch means.

6. The apparatus claimed in claim 5 further comprising a first housing unit for said inductor and a second housing unit for said loading network, said inductor and said loading network connected by a conductor extending between said housing units.

7. The apparatus claimed in claim 6 wherein said manually adjustable member projects from said second housing unit and said second housing unit is provided with indictia for indicating the adjusted position of said member relative to said second housing unit.

8. The apparatus claimed in claim 2 further comprising a first housing unit for said inductor and a second housing unit for said loading network, said inductor and said loading network connected by a conductor extending between said housing units.

9. An eddy current inspection and calibration system comprising:
   a. an eddy current inspection system having a probe for producing electromagnetic fields for inducing eddy currents in a ferrous workpiece passing through the electromagnetic fields, said probe being responsive to changes in the fields caused by eddy current changes for enabling the inspection system to determine the presence of a defect in the workpiece, b. passive flaw simulator circuit means including variable impedance means inductively coupled to said probe for controllably varying the loading of the probe in a manner similar to variations caused by the introduction of a ferrous workpiece having a defect of a known severity into the electromagnetic fields, independently of the coupling to the probe of a portion of workpiece material.

10. The inspection system according to claim 9 further including control circuitry connected to said variable impedance means for controlling the value of impedance of said simulator circuit means.

11. The inspection system according to claim 9 wherein said probe means includes a probe coil and said simulator circuit means comprises:
   a. a reaction coil inductively coupled to said probe coil, and,
   b. a reaction coil loading network connected to said reaction coil, said loading network comprising elements providing a resistive loading for said reaction coil and means for altering said resistive loading.

12. A portable calibrating device usable with a probe assembly of an eddy current inspection system, for simulating a flaw in a ferrous workpiece having a defect of known severity, the calibrating device comprising:
   a. passive non-balanceable workpiece flaw simulator circuitry inductively couplable to a probe assembly and having a resistive component of impedance and an inductive component of impedance, for loading the probe to a first degree independently of coupling to the probe of a portion of workpiece material and,
   b. control means coupled to the workpiece flaw simulator circuitry for selectively varying the value of said resistive component for simulating the effect of a flaw in the ferrous workpiece.

13. The calibration device according to claim 12 wherein said workpiece flaw simulator circuitry comprises a switch for changing the value of said resistive component and said control means includes signal generator means for providing an oscillatory switch signal for controlling the operation of said switch.

14. The calibration device according to claim 12 wherein the simulator circuitry includes a reaction coil for providing said inductive component and an inductor loading network for providing said resistive component, said inductor loading network comprising a switch and a plurality of resistors including a control potentiometer, one resistor of said plurality being controllably connected in said loading network by said switch.

15. Apparatus for simulating workpiece flaws in an eddy current inspection device for controllably varying loading of a detector probe of the eddy current inspection device, the apparatus comprising:
   a. electronic workpiece simulator circuitry electromagnetically couplable to said detector probe, said circuitry including impedance producing elements producing a resistive component and an inductive component operable to load said detector probe in a manner representative of the loading imposed by a defect-free ferrous workpiece independently of coupling to the probe of a portion of workpiece material; and,
   b. control circuitry coupled to said simulator circuitry for varying one of said components to produce a loading change on said detector probe representative of the loading change imposed by moving the probe from the region of an unflawed workpiece to the region of a ferrous workpiece having a defect of known severity.

16. The apparatus according to claim 15 further comprising: housing structure for accommodating said control circuitry and said simulator circuitry for attachment to said detector probe.

17. A method of calibrating without the aid of workpiece material, eddy current inspection systems of the type including probe assemblies operable to produce electromagnetic fields for inducing eddy currents in workpieces being inspected and for responding to alterations in the electromagnetic fields occasioned by the presence of workpiece defects, the method including:
   a. providing passive workpiece flaw simulator circuitry comprising inductor means and impedance producing means connected in circuit with the inductor means,
   b. operating a probe assembly to produce electromagnetic fields,
   c. inductively coupling the inductor means to the probe assembly, independently of the use of workpiece material, and without any initial circuit balancing, and,
   d. passively loading the probe by varying the impedance producing means and simulating the introduction of a ferrous workpiece having a defect of known severity by altering the electromagnetic field to the extent said electromagnetic field would be altered by the presence of a workpiece defect of known severity.

18. The method claimed in claim 17 further including adjustably varying the impedance of said simulator circuitry to control the extent to which said electromagnetic field is altered in order to adjustably vary the severity of the workpiece defect being simulated.

19. A method of calibrating without the aid of workpiece material nondestructive eddy current inspection apparatus of the type having a probe assembly for establishing an electromagnetic field adjacent a workpiece under test to induce eddy currents in the workpiece, said probe assembly being additionally for detecting changes in the eddy currents resulting from a defect in the workpiece appearing in the electromagnetic field, comprising the steps of:
   a. establishing an electromagnetic field with said probe means,
   b. positioning variable impedance electronic workpiece simulator circuitry within said electromagnetic field independently of coupling to the probe of a portion of workpiece material, said circuitry having a first impedance state for establishing a first electromagnetic field condition
   c. altering the impedance state of said workpiece simulator circuitry to a second impedance state to provide a second electromagnetic field condition, the difference between the condition representing the change which would be produced by a ferrous workpiece having a defect of known severity passing through the electromagnetic field, and,
   d. calibrating the inspection apparatus in response to the first and the second electromagnetic field conditions.

20. The method of calibrating according to claim 19 wherein said workpiece simulator circuit provides a resistive component and an inductive component of impedance, and said step of altering includes the step of controllably altering the resistive component of said impedance to provide said second impedance state.

21. The method of calibrating according to claim 19 wherein said step of calibrating comprises the step of calibrating the inspection apparatus according to the change in the electromagnetic field between the first and second field conditions.

22. In a method of calibrating nondestructive eddy current inspection apparatus without the aid of workpiece material, the steps of:
   a. electromagnetically coupling electronic workpiece simulator circuitry to a probe assembly of the inspection apparatus independently of coupling to the probe of a portion of workpiece material, the workpiece simulator circuitry providing an impedance having an inductive component and a resistive component, and,
   b. controllably varying the magnitude of the resistive component of the workpiece simulator circuitry in a predetermined manner to simulate defects in a ferrous workpiece.

23. An eddy current inspection system having apparatus for simulating a flaw in a workpiece for facilitating calibration of the eddy current inspection system, the system including a probe operable to produce electromagnetic fields for inducing eddy currents in the workpiece when present in the region of said fields, the probe being responsive to changes in impedance loading thereof caused by the presence of the workpiece in the field, the workpiece flaw simulator comprising: a first non-balanceable type of circuit means inductively couplable to said probe for impedance loading the probe to a first degree of impedance independently of coupling to the probe of a portion of workpiece material, and second circuitry connected to the first circuit means for altering the effective impedance of the first circuit means as seen by the probe to vary the impedance loading of the probe to simulate the introduction into the field of a ferrous workpiece having a flaw of a predetermined severity.

24. An eddy current inspection system having a workpiece flaw simulator for facilitating calibration of the system, the system including a probe circuit having a coil operable to produce electromagnetic fields for inducing eddy currents in a ferrous workpiece introduced into said fields, the system being responsive to changes in impedance loading of the probe circuit caused by the introduction of the ferrous workpiece in the fields, the flaw simulator comprising:
   a. a first passive non-balanceable circuit including a reaction coil inductively coupled to the probe for loading the probe coil to a first impedance level independently of the introduction of workpiece material into said electromagnetic fields, and
   b. second circuitry connected to said first circuit for altering the effective impedance of said first circuit as seen by said probe coil to vary the loading of the probe coil to simulate the introduction into the fields of a ferrous workpiece having a defect of predetermined severity, said second circuitry comprising: a reaction coil loading network connected to said reaction coil, the network comprising a switch and a plurality of resistors including a control potentiometer, one resistor of said plurality of resistors being controllably connected at any one time in said loading network by said switch, and
   c. housing structure for enclosing said probe and workpiece flaw simulator circuitry.

* * * * *

UNITED STATES PATENT AND TRADEMARK OFFICE
CERTIFICATE OF CORRECTION

PATENT NO. : 4,064,452
DATED : December 20, 1977
INVENTOR(S) : James M. Toth

It is certified that error appears in the above-identified patent and that said Letters Patent are hereby corrected as shown below:

Column 6, line 35, "and" should be -- an --.

Column 10, line 27, "impedence" should be --impedance--;
line 54, "indictia" should be --indicia--.

Column 11, line 26, after "system" delete -- , --.

Column 12, line 13, after "material" delete --, --.

Signed and Sealed this

Second Day of May 1978

[SEAL]

Attest:

RUTH C. MASON
Attesting Officer

LUTRELLE F. PARKER
Acting Commissioner of Patents and Trademarks

UNITED STATES PATENT AND TRADEMARK OFFICE
CERTIFICATE OF CORRECTION

PATENT NO. : 4,064,452
DATED : December 20, 1977
INVENTOR(S) : James M. Toth

It is certified that error appears in the above-identified patent and that said Letters Patent are hereby corrected as shown below:

In Figure 2, an electrical connection point should be regarded as existing between the bottom of the resistor indicated by reference character 60 and the top of the capacitor indicated by reference numeral 66, the top of the resistor 62 and the upper right-hand terminal of the field effect device indicated as 64.

Signed and Sealed this

Twenty-seventh Day of June 1978

[SEAL]

Attest:

RUTH C. MASON
Attesting Officer

DONALD W. BANNER
Commissioner of Patents and Trademarks